United States Patent
Furrer et al.

(10) Patent No.: US 10,391,214 B2
(45) Date of Patent: Aug. 27, 2019

(54) BREAST SHIELD UNIT

(71) Applicant: MEDELA HOLDING AG, Baar (CH)

(72) Inventors: Etienne Furrer, Zug (CH); Mario Rigert, Buchrain (CH); André Schlienger, Maschwanden (CH)

(73) Assignee: MEDELA HOLDING AG, Baar (CH)

( * ) Notice: Subject to any disclaimer, the term of this patent is extended or adjusted under 35 U.S.C. 154(b) by 165 days.

(21) Appl. No.: 14/651,451

(22) PCT Filed: Dec. 12, 2013

(86) PCT No.: PCT/CH2013/000219
§ 371 (c)(1),
(2) Date: Jun. 11, 2015

(87) PCT Pub. No.: WO2014/094186
PCT Pub. Date: Jun. 26, 2014

(65) Prior Publication Data
US 2015/0314053 A1    Nov. 5, 2015

(30) Foreign Application Priority Data

Dec. 18, 2012    (CH) .................................... 2840/12

(51) Int. Cl.
*A61M 1/06*    (2006.01)
*A61M 1/00*    (2006.01)

(52) U.S. Cl.
CPC ............ *A61M 1/064* (2014.02); *A61M 1/066* (2014.02); *A61M 1/0049* (2013.01); *A61M 2205/75* (2013.01)

(58) Field of Classification Search
CPC .............. A61M 1/0049; A61M 1/0066; A61M 1/0064; A61M 1/06; A61M 2205/75
See application file for complete search history.

(56) References Cited

U.S. PATENT DOCUMENTS 3,822,703 A    7/1974    Davisson
5,571,084 A    11/1996    Palmer
(Continued)

FOREIGN PATENT DOCUMENTS

DE    19816776 A1    10/1999
DE    202006019416 U1    3/2007
(Continued)

OTHER PUBLICATIONS

English Translation of International Preliminary Report on Patentability for International Application No. PCT/CH2013/000219, dated Jun. 23, 2015.
(Continued)

*Primary Examiner* — Bhisma Mehta
*Assistant Examiner* — Hamza A Darb
(74) *Attorney, Agent, or Firm* — Marshall, Gerstein & Borun LLP (57) ABSTRACT

A breastshield unit for use with a breastpump for expressing human breastmilk using underpressure has a dimensionally stable breastshield and a flexible breastshield insert for placing in the breastshield. The breastshield has a first, open breastshield end for placing on a mother's breast. The breastshield insert has a first insert end and a second insert end which define a longitudinal direction, the first, open breastshield end having a peripheral edge on which the breastshield insert is securable with the first insert end. In the assembled state, the breastshield insert extends from this first insert end through the inside of the breastshield to the second insert end, wherein the breastshield insert, between the first and second insert ends, extends substantially spaced apart from the breastshield. In the assembled state of the breastshield insert, the second insert end is displaceable in the longitudinal direction relative to the breastshield. The (Continued)

breastshield unit adapts optimally to the shape of the mother's breast and optimizes the bearing force.

19 Claims, 6 Drawing Sheets

(56) References Cited

U.S. PATENT DOCUMENTS

| | | | | |
|---|---|---|---|---|
| 8,070,724 | B2* | 12/2011 | Attolini | A61M 1/0031 604/119 |
| 2003/0004459 | A1* | 1/2003 | McKendry | A61M 1/0066 604/74 |
| 2007/0060873 | A1 | 3/2007 | Hiraoka et al. | |
| 2010/0121267 | A1* | 5/2010 | Silver | A61M 1/06 604/74 |
| 2011/0251552 | A1 | 10/2011 | Brittner | |
| 2012/0083731 | A1 | 4/2012 | Gottenbos et al. | |

FOREIGN PATENT DOCUMENTS

| | | |
|---|---|---|
| EP | 1500408 A1 | 1/2005 |
| EP | 2308523 A1 | 4/2011 |
| WO | WO-2010/054174 A1 | 5/2010 |
| WO | WO-2011/007140 A1 | 1/2011 |
| WO | WO-2011/037841 A2 | 3/2011 |

OTHER PUBLICATIONS

International Search Report for International Application No. PCT/CH2013/000219, dated Jun. 13, 2014.

European Search Report for Application No. EP18153426, dated Apr. 4, 2018.

* cited by examiner

BREAST SHIELD UNIT

CROSS-REFERENCE TO RELATED APPLICATION

The present application is the US national phase of International Patent Application No. PCT/CH2013/000219, filed Dec. 12, 2013, which application claims priority to Switzerland Application No. CH 2840/12, filed Dec. 18, 2012. The priority application, CH 2840/12, is hereby incorporated by reference.

TECHNICAL FIELD

The present invention relates to a breastshield unit and to a breastshield insert.

PRIOR ART

Breastpumps for expressing human breastmilk by means of underpressure are well known. Manually operated breastpumps and motor-driven breastpumps are commercially available. They are connected to a breastshield either directly or via a vacuum line. The breastshield is placed onto the mother's breast from which milk is to be expressed, in such a way that at least the nipple, and in most cases also the areola and the surrounding tissue of the mother's breast, are sealingly enclosed. The breastshield is usually connected to a milk collection container, either directly or via a milk line, such that expressed milk can flow directly into this container.

The known breastshields are substantially rigid funnels, and therefore another funnel has to be chosen according to the size of the breast. Moreover, these breastshields are often used with flexible and soft breastshield inserts in order to enhance the mother's comfort. Some of these inserts have a massaging effect on the breast, in order to promote the flow of milk.

U.S. Pat. No. 5,571,084 discloses a breastshield unit with a hemispherical, stiff shell, and with a flexible breastshield insert arranged in the latter. The breastshield insert has a funnel-shaped main body and a tubular stub formed integrally on the latter. The main body has a peripheral collar turned back over a flange of the shell. The stub is held fixedly in a tubular holder of the shell.

WO 2011/007140 discloses a breastshield unit with a stiff outer breastshield and with a flexible breastshield insert. This insert is also funnel-shaped, with a tubular stub formed integrally thereon, and it is secured at both ends on the breastshield.

WO 2011/037841 describes a breastshield insert on which a duckbill valve is arranged.

DISCLOSURE OF THE INVENTION

It is an object of the invention to make available a breastshield unit and a breastshield insert that are optimally adaptable to the particular shape of the mother's breast and that load or stress the latter as uniformly as possible.

The breastshield unit according to the invention, for use with a breastpump for expressing human breastmilk, has a dimensionally stable breastshield and a flexible breastshield insert for placing in the breastshield. The breastshield has a first, open breastshield end for placing on a mother's breast. The breastshield insert has a first insert end and a second insert end, which define a longitudinal direction, wherein the first, open breastshield end has a peripheral edge, on which the breastshield insert is or can be secured with the first insert end. The breastshield insert, in the assembled state, extends from this first insert end through the inside of the breastshield to the second insert end. The breastshield insert, between the first and second insert ends, extends substantially spaced apart from the breastshield. According to the invention, the second insert end, in the assembled state of the breastshield insert, is displaceable in the longitudinal direction relative to the breastshield.

By virtue of the end of the breastshield insert being displaceable in the longitudinal direction, this breastshield unit conforms optimally to the mother's breast. This adaptation can be further improved by the flexibility and thinness of the breastshield insert. Concerned that the breastshield is not placed tightly enough on the breast, mothers usually press the breastshield too firmly against the breast. Not only is this uncomfortable and painful over a period of time, it also adversely affects the flow of milk. Pressing the breastshield on too tightly is prevented by the breastshield unit according to the invention. The bearing pressure on the breast and the distribution of the bearing pressure are also optimized.

A further advantage is that, by virtue of the adaptability of the breastshield insert, the same shape and size of the breastshield unit and of the breastshield insert is suitable for use within a wide range of different shapes and sizes of breasts. This makes the choice of breastshield unit easier for the mother and reduces the manufacturing costs.

This adaptability to the mother's breast can be enhanced by suitable selection of a breast pad which adjoins the first insert end of the breastshield insert and which has a bearing surface for placing on the mother's breast. For example, this breast pad can be stretched or pretensioned. In addition or alternatively, this breast pad can extend approximately perpendicularly with respect to the longitudinal direction.

The breastshield insert according to the invention preferably has a tubular stub which forms the second insert end. This insert can be produced inexpensively. It is easy to clean thanks to its simple design.

In a preferred embodiment, the breastshield insert according to the invention has a first insert end and, lying opposite the first insert end, a second insert end, which insert ends together define a longitudinal direction. A bearing area for placing on the mother's breast is formed adjacent to the first insert end. A tubular stub for receiving the nipple of the mother's breast is provided. It is formed integrally on the bearing area and extends as far as the second insert end. According to the invention, the bearing surface of the bearing area is approximately flat. The length of the breastshield insert in said longitudinal direction is a multiple of the length of the bearing area in this longitudinal direction.

This breastshield insert is used optimally when its second free end is held displaceably with respect to the breastshield. However, it can also be clamped in place or secured with both ends. The approximately flat bearing surface, particularly if pretensioned in the assembled state, also permits optimized adaptation to different breast sizes and, by virtue of its shape, prevents excessive pressing. This is disclosed here as a further invention.

The second, rear insert end can also be connected non-displaceably to a housing, which is held displaceably in the breastshield. If a housing is present, the latter can be easily moved by hand and helps when placing the unit on the mother's breast.

In a preferred embodiment, a media separation device is also present, which transfers an externally applied vacuum into the interior of the breastshield insert, but which at the same time prevents expressed milk from reaching the vacuum source or passing into any vacuum lines. In this case, the second insert end of the breastshield insert, which forms the abovementioned housing, is preferably connected to the media separation device.

Preferably, the media separation device as a whole is arranged to be movable relative to the breastshield in the longitudinal direction. This too is an independent invention which can also be used in other breastshields without breastshield insert, or without breastshield insert with displaceable second end.

Preferably, the media separation device is suspended on the housing by means of the flexible breast pad. In a preferred embodiment, this suspension is achieved by means of a peripheral securing collar of the breast pad being turned back over a flange of the breastshield.

In a preferred embodiment, the breastshield has guide slits which extend in a longitudinal direction and along which the media separation device as a whole is movable. The movement is guided and limited in this way.

Preferably, the media separation device has a dimensionally stable housing, and a media separation membrane arranged movably therein.

In a preferred embodiment, the breastshield has a rear opening at its second end directed away from the first end, as a result of which the second end of the breastshield insert, and therefore the entire breastshield insert, is manually displaceable in the longitudinal direction towards the mother's breast by access through this rear opening. This makes it easier to apply and adapt the breastshield unit to the mother's breast. The breast pad of the breastshield insert can be pressed forwards out of the breastshield. It can also be turned inside out depending on its shape. If this breast pad is now applied to the breast, it automatically assumes the shape of the breast. Depending on the shape, it then turns back into this shape adapted to the breast.

If a media separation device is present and if the second end of the breastshield insert is connected to this media separation device, then the media separation device can preferably be pressed in or is displaceable manually by access through the open second end of the breastshield.

BRIEF DESCRIPTION OF THE DRAWINGS

Preferred embodiments of the invention are described below with reference to the drawings, which are provided only for explanatory purposes and are not to be interpreted as limiting the invention. In the drawings.

DESCRIPTION OF PREFERRED EMBODIMENTS

Figure 1:
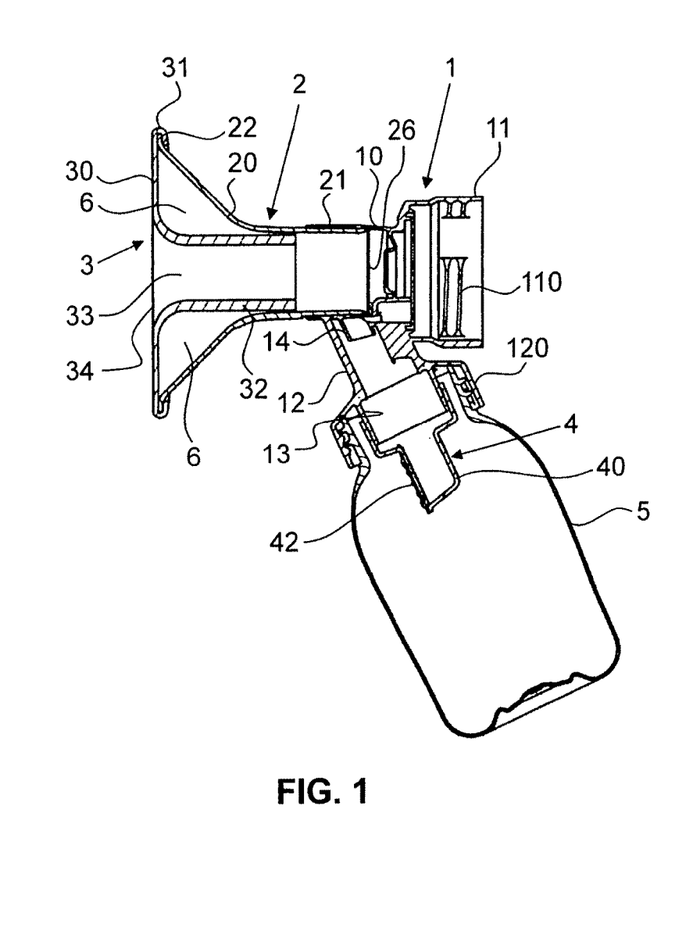
FIG. 1 shows a longitudinal section through a breastshield unit according to the invention, mounted on a milk collection container, in a first embodiment.
Figure 2:
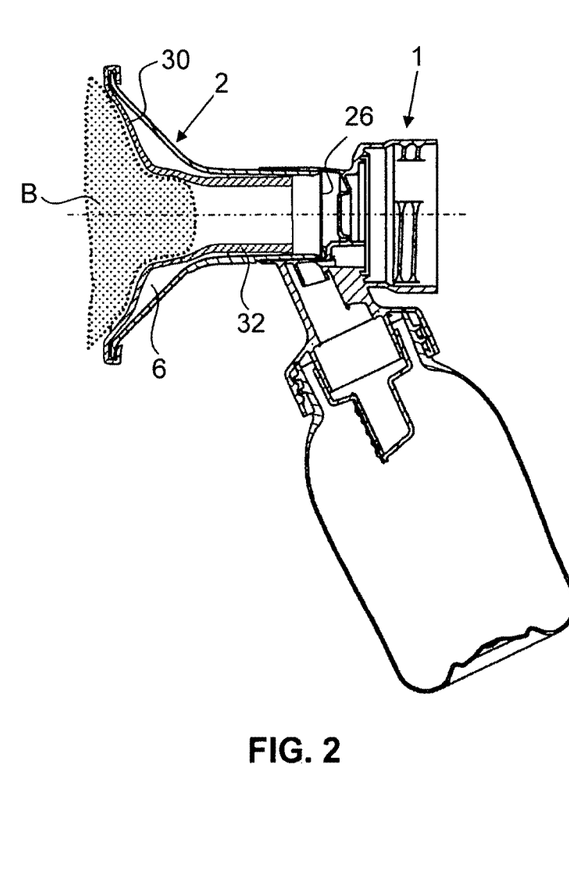
FIG. 2 shows the breastshield unit with milk collection container according to FIG. 1 when placed on a mother's breast.

FIGS. 1 and 2 show a first example of a breastshield unit according to the invention. It has a breastshield 2 and a breastshield insert 3.

The breastshield 2 has a funnel body 20, for receiving a mother's breast B, and a tubular stub 21 preferably formed integrally on said funnel body 20. The breast-side end of the breastshield 2 directed away from the stub 21 is provided with a peripheral and outwardly protruding flange 22. The breastshield 2 is preferably stiff or at least dimensionally stable. It is preferably made of plastic.

The breastshield 2 is held in a coupling part 1. The coupling part 1 has a preferably stiff main body 10 with a tubular holder for the stub 21 of the breastshield 2. A vacuum connector 11 serves for the attachment of a manually driven or motor-driven vacuum pump. Alternatively or in addition, the connector 11 serves for the insertion of a vacuum line, which provides a connection to an external vacuum pump. The vacuum connector 11 can have an inner thread 110 or some other design.

At an angle to this vacuum connector 11, a container attachment part 12 with a milk outlet opening 14 is present and serves for connection to a milk collection container 5. This attachment part 12 also has a connection stub 120 or other suitable connection means. In the interior of the coupling part 1, here in the hollow space of the connection stub 120, a valve is preferably arranged in order to limit the dead volume when expressing milk and in order to prevent a return flow of the expressed milk. In this example, a neck 13 is for this purpose formed integrally on the coupling part 1, on which neck 13 a valve unit 4 with a valve body 40 and a valve membrane 42 can be secured.

The coupling part 1 and the milk collection container 5 can also have a different design. The coupling part 1 can also be a component of the breastshield 2, as is shown, for example, in the example described further below. Here, a one-part or multi-part unit of coupling part 1 and breastshield 2 can be formed.

Figure 3:
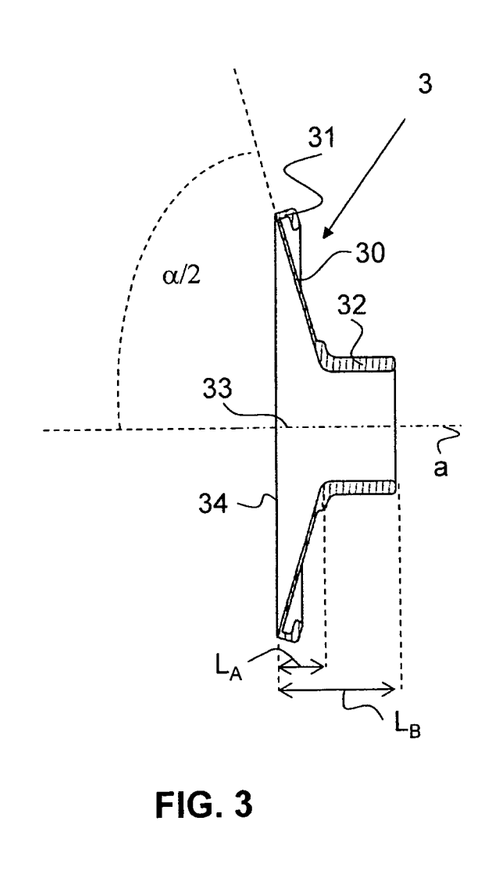
FIG. 3 shows a longitudinal section through a breastshield insert according to the invention.

The breastshield insert 3 is made from a soft, elastic and flexible material, preferably from silicone. It has a breast pad 30 with a receiving opening 33 for bearing on the mother's breast B, and a stub 32 formed integrally on said breast pad 30. The receiving opening 33 leads from the breast-side end of the insert 3, by way of a channel through the stub 32, to the end of the insert 3 directed away from the breast. This defines a longitudinal direction a, which is indicated in FIG. 3.

On a breast-side, first insert end 34 of the insert 3 directed away from the stub 32, a securing collar 31 is integrally formed, which can be turned back over the flange 22 of the breastshield 2. In this way, the breastshield insert 3 can be secured on the breastshield 2.

The stub 32 of the breastshield insert 3 is pushed into the stub 21 of the breastshield 2. However, its external diameter is such that it slides inside this stub 21 and is therefore not fixed. The stub 32 of the breastshield insert 3 thus forms a second insert end, which is held displaceably with respect to the breastshield 2.

In FIG. 1, the breastshield unit is shown in the assembled state, but before use or when not currently in use. In this state, a peripheral hollow space 6 is present between breastshield 2 and breastshield insert 3, i.e. the breastshield insert 3, or at least the breast pad 30 and the uninserted part of the stub 32, extends at a distance from the inner wall of the breastshield 2. The breast pad 30 is approximately flat, or it has a funnel shape with a relatively large opening angle α of 100 to 150°. The breast pad 30 is preferably stretched or pretensioned in the breastshield 2. That is to say, in the unassembled state it preferably has an opening angle α of 120° to 180°, and in the assembled state it is approximately flat or is stretched or pretensioned as far as the abovementioned opening angle.

In FIG. 2, the breastshield unit is shown in the state when in use. The breast pad 30 is placed on a mother's breast B, with the nipple protruding into the receiving opening 33. By pressing the breastshield unit onto the breast B, the breast pad 30 deforms and adapts to the shape of the breast B. It adopts in particular, but not exclusively, a funnel shape and/or a concave shape. If the pressure is too great, the breastshield insert 3 moves rearwards, i.e. away from the breast B, by means of the stub 32 moving relative to the breastshield 2, and therefore to the front fastening of the insert 3 in the breastshield 2, and approaching a rear end 26 of the breastshield 2. The tight bearing of the insert 3 on the breast B is still ensured even when the bearing pressure is reduced.

Figure 4:
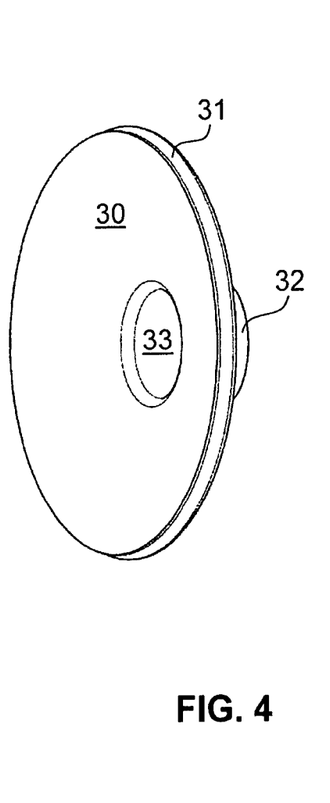
FIG. 4 shows a perspective view of the breastshield insert according to FIG. 3 from the front.
Figure 5:
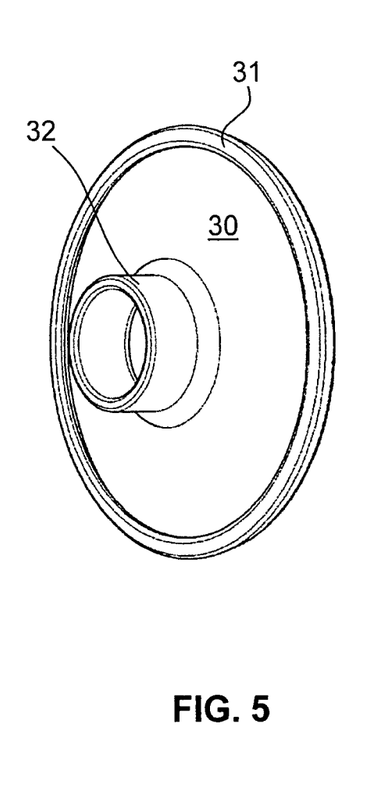
FIG. 5 shows a perspective view of the breastshield insert according to FIG. 3 from the back.

A breastshield insert 3 of this kind is shown in FIGS. 3 to 5. It corresponds substantially to the one shown in FIGS. 1 and 2, but its stub 32 is shorter. Moreover, the breast pad 30 has a lesser wall thickness than the stub 32. The stub 32 is preferably more or less dimensionally stable, and the breast pad 30 is like a membrane and therefore more flexible and more elastic than the stub 32. The breast pad 30 and the receiving opening 33 are preferably circular. The breast pad 30 is preferably completely flat, and its rear face, i.e. the face directed away from the breast, also preferably has no elevations or depressions. The breast pad 30 has a length $L_A$, which is many times shorter than the length $L_B$ of the whole insert 3.

FIGS. 6 to 12 show another illustrative embodiment. Identical parts are provided with the same reference signs as in the first example.

In this embodiment, the breastshield 2 has a housing-shaped main body 25. The breastshield 2 serves to bear on the mother's breast B, but also at the same time to connect to the milk collection container 5. For this purpose, it has a milk attachment part 28 with which it can be connected to the milk collection container 5. The breastshield 2 is preferably stiff or dimensionally stable and is in particular made of plastic.

The main body 25 accommodates a media separation device 7, which here serves for media separation and for connection to the breastshield insert 3 and to the vacuum pump (not shown). Media separation devices for breastpumps are known from the prior art. They serve to protect the vacuum pump from being contaminated by milk.

The media separation device 7 according to FIGS. 6 to 12 has a housing 70, which is preferably stiff or dimensionally stable and is in particular made of plastic. In the rear area directed away from the breast B, a vacuum connector 71 is present for connection to a vacuum pump or to a vacuum line.

Figure 6:
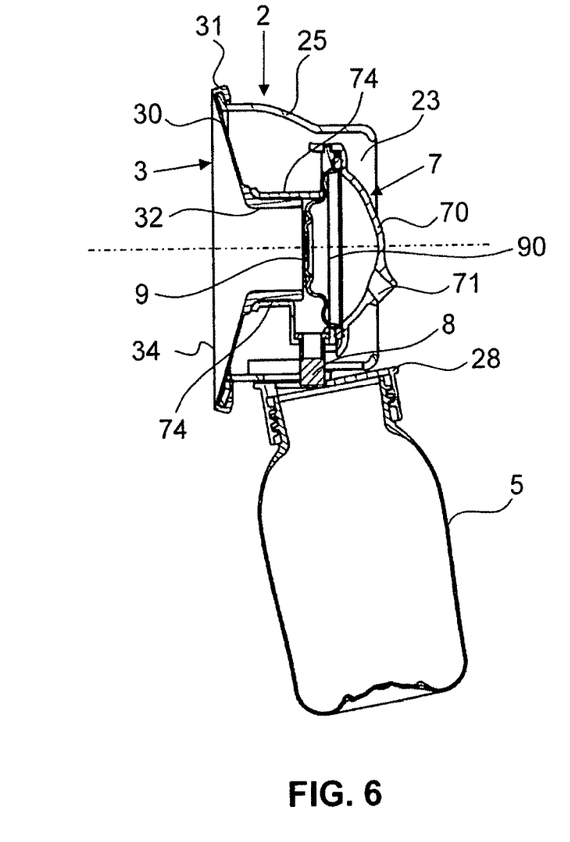
FIG. 6 shows a longitudinal section through a breastshield unit according to the invention, mounted on a milk collection container, in a second embodiment.
Figure 7:
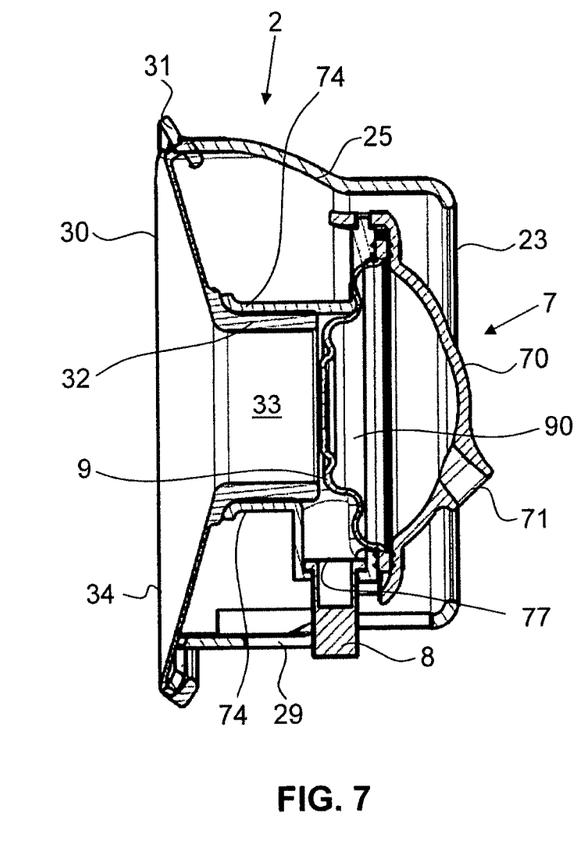
FIG. 7 shows the breastshield unit according to FIG. 6 in an enlarged view.

A milk outlet opening 77, which is provided with a nonreturn valve 8, leads into the milk collection container 5 by way of a through-opening 29 of the main body 25.

A breastshield insert holder 74 is formed integrally on the housing 70 of the media separation device 7 and forms a receiving stub for the stub 32 of the insert 3. The stub 32 of the insert 3 is held non-displaceably in this holder 74 during use. It is held with an interference fit, for example, and can be removed for cleaning or replacement. However, it can also be connected to the media separation device 7 such that it cannot be released without destruction. The first insert end 34 of the insert 3 is once again turned back over the flange 22 of the main body 25 of the breastshield 2. The insert 3 is preferably designed according to the illustrative embodiment shown in FIGS. 3 to 5 or in the above-described sense according to the invention. In all of the illustrative embodiments, the insert 3 preferably has a maximum external diameter that is slightly smaller than the maximum external diameter of the breastshield 2. The securing collar 31 preferably has a smaller diameter than the flange 22 of the breastshield 2. In this way, the insert 3 is stretched when secured on the breastshield 2.

For the purpose of media separation, the media separation device 7 has a media separation membrane 9. The latter is held movably in the housing 70. It forms a pump chamber 90 with the rear wall of the housing 70. When an underpressure is conveyed cyclically into the pump chamber via the vacuum connector 71, the media separation membrane 9 moves synchronously with this and transfers the underpressure into the hollow space formed by the breastshield insert 3 and the mother's breast B. Milk is expressed. The media separation membrane 9 prevents expressed milk from passing into the pump chamber 90 and from there to the vacuum source. Instead, the milk flows through the milk outlet opening 77, arranged before the membrane 9, into the milk collection container 5.

Figure 9:
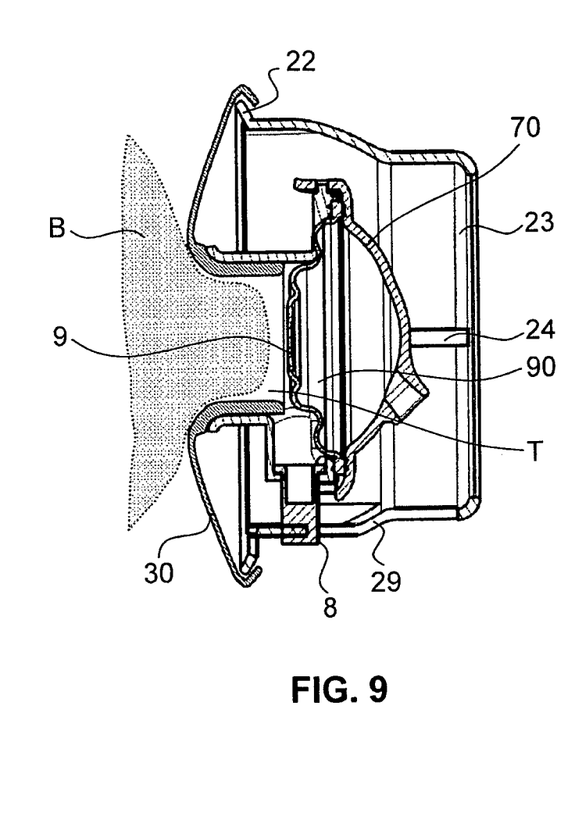
FIG. 9 shows the breastshield unit according to FIG. 7 being placed on a mother's breast.
Figure 11:
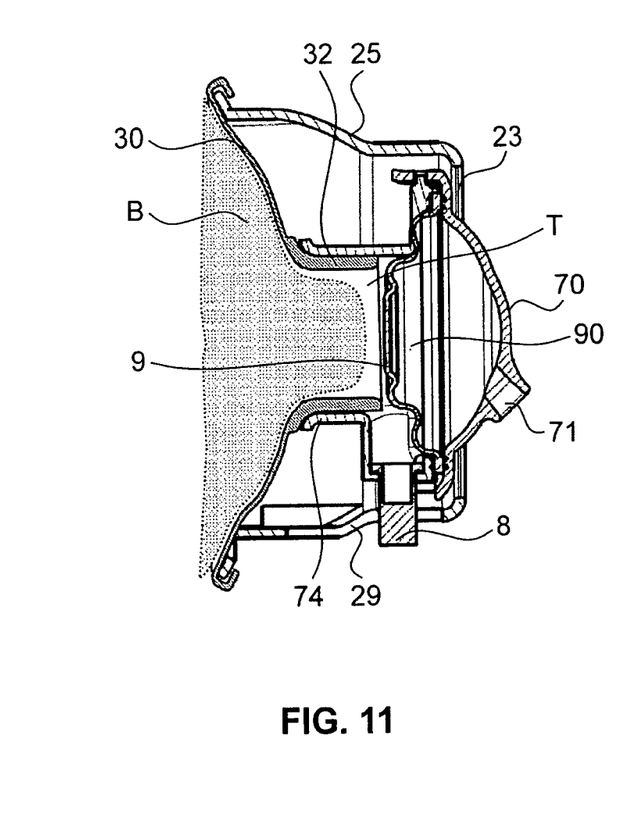
FIG. 11 shows the breastshield unit according to FIG. 7 when placed on a mother's breast.
Figure 12:
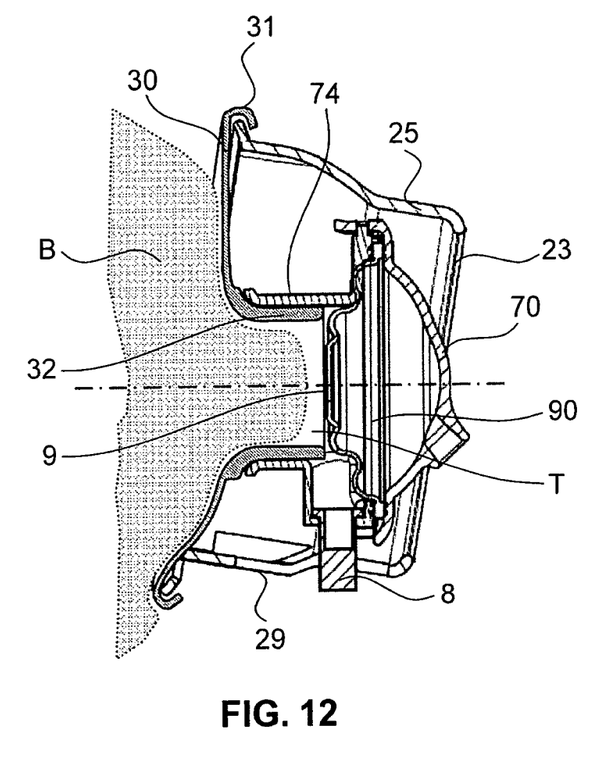
FIG. 12 shows the breastshield unit according to FIG. 7 in an inclined position.

The media separation membrane 9 is preferably located, at least in the undeflected starting state, in the bearing area of the nipple. This optimally minimizes the dead volume T. As can be seen in FIG. 9, the media separation membrane 9, even in the undeflected state, reaches approximately or exactly as far as the end of the stub 32 of the insert 3. It will be seen in FIG. 11 that the stub 32 is dimensioned in such a way that, with a breast and nipple of a size in the normal range, it is filled along its entire length by the nipple. However, during the expression of milk, the media separation membrane 9 preferably does not touch the nipple, and instead they move synchronously in the same direction. FIG. 12 shows an inclined position, which can be obtained by suitably shaped guide slits 24.

According to the invention, the media separation device 7 is movable, in particular displaceable in the main body 25 of the breastshield 2. For this purpose, the main body 25 has guide slits 24, in which guide lugs 76 of the housing 70 engage. This can be seen in FIG. 8, for example. The media separation device 7 is displaceable along these slits 24. The slits 24 can be rectilinear or curved. They are rectilinear in this example. The valve 8 and the milk outlet opening 77 lead into the milk collection container 5 in all positions of the media separation device 7 relative to the main body 25, since the through-opening 29 is larger than the valve 8 and the milk outlet opening 77. The through-opening 29 is preferably designed as an oblong hole.

The rear end of the main body 25, directed away from the breast, is open. The media separation device 7 is manually movable via this rear opening 23, specifically displaceable in this case along the slits 24.

Figure 8:
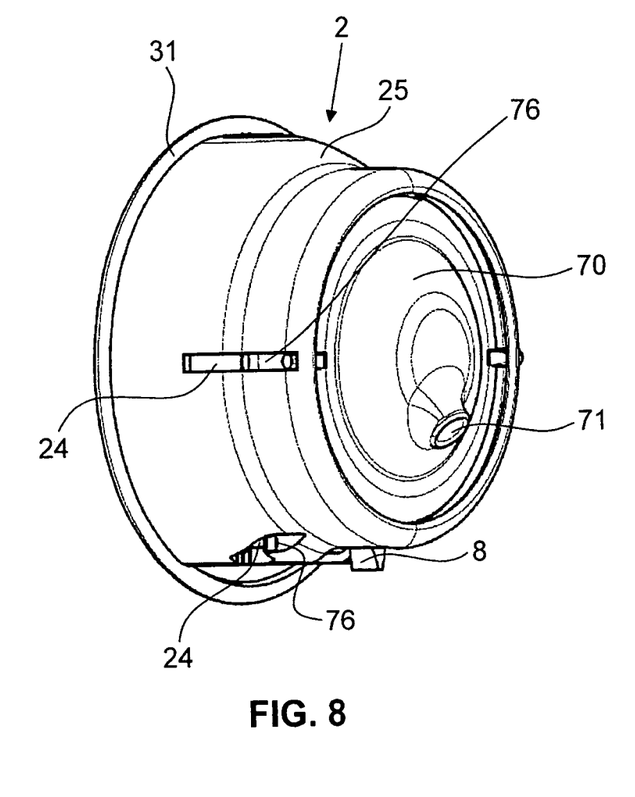
FIG. 8 shows a perspective view of the breastshield unit according to FIG. 6 in a first position.

In FIGS. 7 and 8, the breastshield unit is shown in the state before use or when not currently in use. The media separation device 7 protrudes through the rear opening 23 or is located at least in a rear area. The breast pad 30 of the insert 3 is relaxed and is slightly funnel-shaped in this example.

Figure 10:
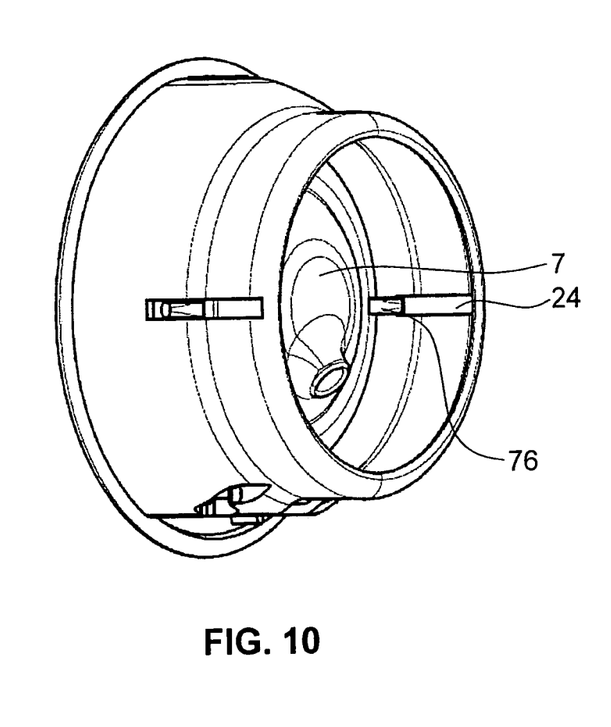
FIG. 10 shows a perspective view of the breastshield unit in the position according to FIG. 9.

In order to use the breastshield unit, the media separation device 7 is pushed forwards by hand, as is shown in FIGS. 9 and 10. The breast pad 30 of the insert 3 is prestressed, being pushed out to the front, according to requirements, towards the mother's breast B. The nipple can be received optimally in the receiving opening 33. If the manual pressure on the housing 70 is now stopped, but the main body 25 is held as before on the breast by hand, in a bra or another holding device, the housing 70 slides back along the slits 24 and the insert 3 lies sealingly, but without excessive or unevenly distributed pressure, on the breast B. This is shown in FIG. 11. Expressing milk can now begin.

In this example too, the second insert end is therefore displaceable relative to the breastshield 2, this displacement taking place together with the media separation device 7. Instead of the media separation device, the second insert end can also be held in another part that is displaceable relative to the breastshield. For example, the housing 70 can be designed in the same way as described above, or similarly, and be held in the breastshield 2, but have no media separation membrane 9.

The breastshield unit according to the invention adapts optimally to the shape of the mother's breast and optimizes the bearing force.

The invention claimed is:

1. A breastshield unit for use with a breastpump for expressing human breastmilk by means of underpressure, comprising a dimensionally stable breastshield and a flexible breastshield insert for placing in the breastshield, the breastshield having a first, open breastshield end for placing on a mother's breast, the breastshield insert having
    a first insert end,
    a second insert end,
    a bearing area for placing on a mother's breast, the bearing area adjoining the first insert end and comprising a receiving opening leading from the first insert end to the second insert end,
    and a tubular stub formed integrally on the bearing area and extending as far as the second insert end, the first and second insert ends together defining a longitudinal direction,
    the first, open breastshield end having a peripheral edge, on which the breastshield insert is securable with the first insert end,
    the breastshield insert, in an assembled state, extending from the first insert end through an inside of the breastshield to the second insert end,
    the breastshield insert, between the first and second insert ends, extending substantially spaced apart from the breastshield,
    and, in the assembled state of the breastshield insert, the second insert end is displaceable in the longitudinal direction relative to the breastshield, to adapt the breastshield insert to a shape of the breast and to provide a bearing force,
    wherein the bearing area extends approximately perpendicularly with respect to the longitudinal direction before being applied to the mother's breast and wherein the bearing area is approximately flat before being applied to the mother's breast, wherein the bearing area adapts to the shape of the mother's breast when applied to the mother's breast.

2. The breastshield unit according to claim 1, wherein the bearing area is stretched or pretensioned.

3. The breastshield unit according to claim 1, wherein the breastshield has a rear opening at a second end of the breastshield directed away from the first, open breastshield end, as a result of which the second insert end is manually displaceable in the longitudinal direction towards the mother's breast by access through the rear opening.

4. The breastshield unit according to claim 1, wherein the second insert end is connected to a media separation device, which transfers an externally applied vacuum into an interior of breastshield insert.

5. The breastshield unit according to claim 4, wherein the media separation device as a whole is arranged to be movable relative to the breastshield in the longitudinal direction.

6. The breastshield unit according to claim 5, wherein the breastshield has guide slits which extend in the longitudinal direction and along which the media separation device as a whole is movable.

7. The breastshield unit according to claim 4, wherein the media separation device has a dimensionally stable housing and a media separation membrane arranged movably therein.

8. The breastshield unit according to claim 3, wherein the breastshield has a rear opening at the second end of the breastshield directed away from the first, open breastshield end, as a result of which the media separation device is manually displaceable towards the breast in the longitudinal direction by access through the rear opening.

9. A flexible breastshield insert for use with a breastpump for expressing human breastmilk by means of underpressure, wherein the breastshield insert has
    a first insert end,
    a second insert end lying opposite the first insert end, the first insert end and the second insert end together defining a longitudinal direction,
    a bearing area for placing on a mother's breast and, the bearing area adjoining the first insert end and comprising a receiving opening leading from the first insert end to the second insert end,
    and a tubular stub for receiving a nipple of the mother's breast, the tubular stub being formed integrally on the bearing area and extending as far as the second insert end, wherein the bearing area extends approximately perpendicularly with respect to the longitudinal direction before being applied to the mother's breast and wherein the bearing area is approximately flat before being applied to the mother's breast, wherein the bearing area adapts to a shape of the mother's breast when applied to the mother's breast and wherein a length of the breastshield insert in said longitudinal direction is at least twice of a length of the bearing area in the longitudinal direction.

10. The breastshield insert according to claim 9 for use in a breastshield unit with a breastpump for expressing human breastmilk by means of underpressure, the breastshield unit comprising a dimensionally stable breastshield and the breastshield insert, the breastshield insert being disposed in the breastshield, the breastshield having a first, open breastshield end for placing on the mother's breast, the first, open breastshield end having a peripheral edge, on which the breastshield insert is securable with the first insert end, the breastshield insert, in an assembled state, extending from the first insert end through an inside of the breastshield to the second insert end, the breastshield insert, between the first and second insert ends, extending substantially spaced apart from the breastshield, and, in the assembled state of the breastshield insert, the second insert end being displaceable in the longitudinal direction relative to the breastshield, to adapt the breastshield insert to the shape of the breast and to provide a bearing force.

11. The breastshield insert according to claim 9, and further comprising a housing in which the second insert end is held non-displaceably, wherein the housing is designed to be held movably in a breastshield.

12. The breastshield insert with the housing according to claim 11, wherein the housing is part of a media separation device with a media separation membrane.

13. A breastshield unit for use with a breastpump for expressing human breastmilk by means of underpressure comprising a dimensionally stable breastshield and a flexible breastshield insert for placing in the breastshield, the breastshield having a first, open breastshield end for placing on a mother's breast, the breastshield insert having a first insert end and a second insert end, the first and second insert ends together defining a longitudinal direction, the first, open breastshield end having a peripheral edge, on which the breastshield insert is securable with the first insert end, the breastshield insert, in an assembled state, extending from the first insert end through an inside of the breastshield to the second insert end, and the breastshield insert, between the first insert end and the second insert end, extending substantially spaced apart from the breastshield, wherein, in the assembled state of the breastshield insert, the second insert end is displaceable in the longitudinal direction relative to the breastshield, wherein the second insert end is connected to a media separation device, which transfers an externally applied vacuum into an interior of the breastshield insert, wherein the media separation device as a whole is arranged to be movable relative to the breastshield in the longitudinal direction, thereby adapting the breastshield insert to a shape of the breast and providing a bearing force.

14. The breastshield unit according to claim 13, wherein the breastshield has a second breastshield end and wherein the breastshield has a rear opening at the second breastshield end directed away from the first breastshield end, as a result of which the second insert end is manually displaceable in the longitudinal direction towards the mother's breast by access through the rear opening.

15. The breastshield unit according to claim 13, wherein the breastshield has guide slits which extend in the longitudinal direction and along which the media separation device as a whole is movable.

16. The breastshield unit according to claim 13, wherein the media separation device has a dimensionally stable housing and a media separation membrane arranged movably therein.

17. The breastshield unit according to claim 16, wherein the second insert end is held non-displaceably in the housing.

18. The breastshield unit according to claim 13, wherein the breastshield insert has a tubular stub, which forms the second insert end.

19. The breastshield unit according to claim 13, wherein the breastshield insert has a length in said longitudinal direction, the length being at least twice of a length of a bearing surface in the longitudinal direction.

* * * * *

UNITED STATES PATENT AND TRADEMARK OFFICE
CERTIFICATE OF CORRECTION

PATENT NO. : 10,391,214 B2
APPLICATION NO. : 14/651451
DATED : August 27, 2019
INVENTOR(S) : Etienne Furrer et al.

Page 1 of 1

It is certified that error appears in the above-identified patent and that said Letters Patent is hereby corrected as shown below:

In the Claims

At Column 8, Line 25, "claim 3," should be -- claim 4, --.

Signed and Sealed this
Seventh Day of April, 2020

Andrei Iancu
*Director of the United States Patent and Trademark Office*